United States Patent [19]

Vadino

[11] Patent Number: 4,777,050

[45] Date of Patent: Oct. 11, 1988

[54] CONTROLLED-RELEASE DOSAGE FORM COMPRISING ACETAMINOPHEN, PSEUDOEPHEDRINE AND DEXBROMPHENIRAMINE

[75] Inventor: Winston A. Vadino, Whitehouse Station, N.J.

[73] Assignee: Schering Corporation, Kenilworth, N.J.

[21] Appl. No.: 29,032

[22] Filed: Mar. 23, 1987

[51] Int. Cl.[4] .................. A61K 31/74; A61K 9/20; A61K 9/22

[52] U.S. Cl. .................................. 424/468; 424/436; 424/480; 424/488; 424/493; 424/499; 514/781

[58] Field of Search ............... 424/468, 436, 480, 488, 424/493, 499; 514/781

[56] References Cited

U.S. PATENT DOCUMENTS

| | | | |
|---|---|---|---|
| 4,389,393 | 6/1983 | Schor et al. | 424/19 |
| 4,601,894 | 7/1986 | Hanna et al. | 424/19 |
| 4,657,757 | 4/1987 | Hanna et al. | 424/488 |
| 4,695,591 | 9/1987 | Hanna et al. | 514/781 |

Primary Examiner—Michael R. Lusignan
Attorney, Agent, or Firm—Anita W. Magatti; Stephen I. Miller; James R. Nelson

[57] ABSTRACT

The invention relates to a controlled release dosage form comprising three actives: acetaminophen, pseudoephedrine and dexbrompheniramine.

20 Claims, No Drawings

CONTROLLED-RELEASE DOSAGE FORM COMPRISING ACETAMINOPHEN, PSEUDOEPHEDRINE AND DEXBROMPHENIRAMINE

SUMMARY OF THE INVENTION

The present invention relates to an oral controlled-release matrix dosage form which combines three pharmaceuticals, acetaminophen, pseudoephedrine or a pharmaceutically acceptable salt thereof and dexbrompheniramine or a pharmaceutically acceptable salt thereof, one or more polymers, and excipients.

BACKGROUND OF THE INVENTION

Acetaminophen is a well-known analgesic and antipyretic which reduces the discomfort and fever due to colds and other viral infections.

Pseudoephedrine and pharmaceutically acceptable salts thereof, e.g. the sulfate and the hydrochloride, are well-known decongestants which restore freer breathing by shrinking nasal passages and promote sinus drainage in those suffering from colds, allergies or sinusitis.

Dexbrompheniramine and pharmaceutically acceptable salts thereof, e.g. the maleate, are well-known antihistamines which provide relief of the pruritis, rhinitis and sneezing associated with colds and allergies.

Controlled-release dosage forms which comprise a single active component are well known, including matrix tablet systems incorporating active ingredients, lubricants, binders, fillers and other excipients, wherein the binders may be hydrophilic, hydrophobic or water-insoluble polymers; see for example U.S. Pat. No. 4,389,393. However, controlled-release dosage forms which combine two actives are not common, and but for U.S. Pat. No. 4,601,894 and U.S. Pat. No. 4,657,757, wherein hydroxypropyl methylcellulose must be present as a binder, no controlled-release dosage forms combining three actives in a single uniform dosage form are known because of the difficulties encountered in combining multiple actives, each with different chemical and physical characteristics, different release rates, different half-lives and different dosage sizes.

The mechanism by which controlled-release dosage forms act to dispense the active ingredients over a period of time have been described at length in the literature; see for example Manford Robinson, Chapter 14, "Sustained Action Dosage Forms", *The Theory and Practice of Industrial Pharmacy*, 2nd. ed., ed. L. Lachman, H. Lieberman and J. Kanig (Philadelphia; Lea & Febiger, 1976).

DETAILED DESCRIPTION OF THE INVENTION

The controlled-release dosage form which is the subject of this invention presents a novel advancement of the art since it combines three active ingredients, acetaminophen, pseudoephedrine or a pharmaceutically acceptable salt thereof, preferably pseudoephedrine sulfate, and dexbrompheniramine or a pharmaceutically acceptable salt thereof, preferably dexbrompheniramine maleate, in a single long-acting tablet. While antihistamines and decongestants have been combined in controlled release tablets, and while antihistamines, decongestants and analgesics have been combined in two-layer tablets or have been separately microencapsulated and combined in continuous-action capsules, the present invention relates to a surprisingly simple combination of three actives in a single homogeneous matrix, from which matrix each active component is released at an appropriate rate to provide the desired activity over a period of 2–14, preferably 8–12 hours.

The components of the matrix are preferably chosen so that a dosage form of the present invention releases the actives over a period of 12 hours.

It is most unexpected that each active component is released from the matrix at its desired rate despite the differences in solubilities among the actives in gastric or aqueous media, indicating that different mechanisms of drug release, i.e. diffusion through and erosion of the hydrated layer, are occurring simultaneously. Another unexpected feature is that the differences in dosage size do not affect the appropriate release of each of the actives. That is, acetaminophen, pseudoephedrine and dexbrompheniramine may be present at an approximate weight ratio of 200:20:1, for example, and the desired sustained release rates for each are still obtained. It is also unexpected that each one of three actives with significantly different biological half-lives should demonstrate its own efficacious pharmacological profile when combined in a single sustained-release dosage form.

The specific preferred combination of actives of the invention, i.e. acetaminophen, pseudoephedrine sulfate and dexbrompheniramine maleate, presents an advantage to cold and allergy sufferers by providing a single sustained-release medicament with antihistaminic, decongestant and analgesic properties. Thus, repeated administration of several single-component dosage forms throughout the day may be avoided. Moreover, it is apparent that, in addition to the well-known pharmacological advantages of a controlled-release formulation in general (e.g. more constant blood levels of the drugs), the dosage form of the present invention is easier and more economical to manufacture than microencapsulated or multi-layered dosage forms.

Although the three actives and one or more polymers must always be present in the dosage form of the invention, the concentrations of the actives and polymer may vary. For the filler and other excipients, the nature as well as each concentration of the component may also vary.

Acetaminophen may be present at from 400 to 750 mg/tablet, preferably 500 mg/tablet. Pseudoephedrine sulfate may be present at from 15 to 75 mg/tablet, preferably 60 mg/tablet. Dexbrompheniramine maleate may be present in the range of 1 to 5 mg/tablet, with 3 mg/tablet being preferred.

While a number of polymers might be used as binder for the matrix, this invention particularly contemplates the use of cellulosic polymers selected from methylcellulose, hydroxypropylcellulose, hydroxymethylcellulose, hydroxyethylcellulose, carboxymethylcellulose, carboxyethylcellulose, sodium carboxymethylcellulose and sodiumcarboxyethyl cellulose or combinations of said cellulosic polymers and ethylcellulose or other cellulose ethers. A single cellulosic polymer may be used, or a mixture of cellulosic polymers of different molecular weight and structure may be used. Where the cellulosic polymer is combined with a cellulose ether, a combination of a cellulosic polymer and ethylcellulose is preferred. The cellulosic polymers are commercially available in a variety of grades, particle sizes and/or viscosities. Preferred cellulosic polymers are hydroxypropylcellulose and hydroxyethylcellulose.

Of the total polymer weight, 100–55% may be a cellulosic polymer or a mixture of cellulosic polymers and 0–45% may be a cellulose ether, preferably ethylcellulose. For dual polymer systems, e.g. wherein 99–55% of the total polymer weight may be a cellulosic polymer or a mixture of cellulosic polymers and 1–45% may be a cellulose ether, preferred ranges of polymer weight are 66.5–55% cellulosic polymer and 33.5–45% cellulose ether. When only a cellulosic polymer or a mixture of cellulosic polymers is used, the total polymer content represents 1–8% by weight of the dosage form (i.e., the uncoated core dosage form), and for a dual system the total polymer content represents 8–15% by weight of the dosage form. A preferred range for the total amount of polymer present for the single polymer system is 6–6.5% by weight of the dosage form, and for the dual polymer system the preferred range is 11.5–12.5%. In a preferred embodiment, only one cellulosic polymer is used, i.e. 100% cellulosic polymer, preferably hydroxypropyl cellulose or hydroxyethyl cellulose. Another preferred embodiment is a dual polymer system having a total polymer weight of 11.5–12.5% of the dosage form and comprising about 55–60% cellulosic polymer and about 40–45% cellulose ether.

Also present in the matrix are one or more fillers such as dibasic calcium phosphate dihydrate or lactose, with dibasic calcium phosphate dihydrate being preferred. The filler is present in a amount to 10–13% of the total dosage form weight, with about 12% being preferred.

When the weight of the polymer component is varied, corresponding variations in the filler weight are made in order to maintain constant tablet weight and controlled-release profile.

The matrix also preferably contains one or more lubricating agents, e.g. stearic acid, magnesium stearate, calcium stearate, waxes, polyethylene glycol, or magnesium lauryl sulfate, present in an amount of 1–3% of the total dosage-form weight. A preferred embodiment comprises 0.9 to 1.7% stearic acid and 0.25 to 0.78% magnesium stearate.

Other excipients, such as disintegrating agents, coloring agents and flavorings, may be added at the discretion of those skilled in the art.

The above components are combined to form the matrix and formed into tablets by conventional means (see Example 1). The tablets may be used as such, but are preferably coated by techniques well known in the art. An example of such a tablet coating is shown in Example 1.

The following Examples describe typical batch and single tablet formulas of the controlled-release dosage forms of this invention.

EXAMPLE 1

Tablet Cores

| Ingredients | Approximate g/Batch | mg/tablet |
| --- | --- | --- |
| Acetaminophen USP 90% (I) | 66,600* | 555*** |
| Pseudoephedrine Sulfate USP (II) | 7,200 | 60 |
| Dexbrompheniramine Maleate USP (III) | 369** | 3 |
| Hydroxypropylcellulose | 5,760 | 48 |
| Dibasic Calcium Phosphate Dihydrate USP | 11,400 | 95 |
| Stearic Acid NF | 1,200 | 10 |
| Magnesium Stearate NF | 480 | 4 |
| Purified Water USP (evaporates) | — | — |
| Alcohol 3A SD (evaporates) | — | — |
| Approximate Batch Weight (g) | 93,000 | 775 |
| Approximate Core Yield (cores) | 120,000 | |

*Equivalent to 60,000 g of Acetaminophen.
**Up to a 5% manufacturing overcharge may be added with compensating adjustments in the core weight, the amount of filler or both.
***Equivalent to 500 mg Acetaminophen.

Method of Manufacture

Blend I, II, dicalcium phosphate dihydrate and hydroxypropylcellulose for 5–30 minutes in a suitable mixer. Dissolve III in acqueous alchol and use it to granulate the powder blend. Dry and mill the granulation using a suitable size screen. Add the remaining ingredients and blend for 3–15 minutes. Compress into suitable size tablets.

Tablet Coating

| Ingredients | Approximate g/Batch | mg/tablet |
| --- | --- | --- |
| Hydroxypropyl Methylcellulose 2910 or 2906 USP | 1,440 | 12 |
| Polyethylene glycol 3350 NF | 300 | 2.5 |
| Methyl p-hydroxybenzoate NF | 14.4 | 0.12 |
| Propyl p-hydroxybenzoate NF | 10.8 | 0.09 |
| Purified Water USP (evaporates) | (1) | — |
| Coloring Agent | (2) | — |

(1) Sufficient amounts of Purified Water are used as required in the coating process.
(2) An appropriate amount of a coloring agent (e.g. color dispersion solids) may be added.

Method of Manufacture

Prepare polymer solution using standard methods. Combine polymer solution with coloring agent (in dispersion) and sufficient water. Coat tablets with colored polymer solution and polish the coated tablets using standard procedures.

EXAMPLE 2

Tablet Cores

| Ingredients | Approximate g/Batch | mg/tablet |
| --- | --- | --- |
| Acetaminophen USP | 60,000 | 500 |
| Pseudoephedrine sulfate USP | 7,200 | 60 |
| Dexbrompheniramine Maleate USP | 369* | 3 |
| Hydroxypropylcellulose | 6,300 | 52.5 |
| Ethylcellulose NF | 4,500 | 37.5 |
| Dibasic Calcium Phosphate Dihydrate USP | 10,080 | 84 |
| Stearic Acid NF | 1,140 | 9.5 |
| Magnesium Stearate NF | 420 | 3.5 |
| Purified Water USP (evaporates) | — | — |
| Alcohol 3A SD (evaporates) | — | — |
| Approximate Batch Weight (g) | 90,009 | 750 |
| Approximate Core Yield (cores) | 120,000 | |

*Up to a 5% manufacturing overcharge may be added with compensating adjustments in the core weight or amount of filler or both.

Method of Manufacture

Blend I, dicalcium phosphate dihydrate, II and hydroxypropylcellulose in a suitable mixer for 5–30 minutes. Dissolve III and ethylcellulose in 3A alcohol and use it to granulate the powder blend. Dry and mill the granulation using a suitable size screen. Add remaining ingredients and blend for 3-15 minutes. Compress into suitable size tablets.

The tablet cores may be coated in a manner similar to that described in Example 1.

EXAMPLE 3

Tablet Cores

| Ingredients | Approximate g/Batch | mg/tablet |
|---|---|---|
| Acetaminophen USP 90% | 66,600* | 555*** |
| Pseudoephedrine Sulfate USP | 7,200 | 60 |
| Dexbrompheniramine Maleate USP | 369** | 3 |
| Hydroxyethylcellulose | 5,760 | 48 |
| Dibasic Calcium Phosphate Dihydrate USP | 11,400 | 95 |
| Stearic acid NF | 1,200 | 10 |
| Magnesium Stearate NF | 480 | 4 |
| Purified Water USP (evaporates) | — | — |
| Alcohol 3A SD (evaporates) | — | — |
| Approximate Batch Weight (g) | 93,000 | 775 |
| Approximate Core Yield (cores) | 120,000 | |

*Equivalent to 60,000 g of Acetaminophen.
**Up to 5% manufacturing overcharge may be added with compensating adjustments in the core weight, the amount of filler, or both.
***Equivalent to 500 mg Acetaminophen

Method of Manufacture

Prepare tablets as described in Example 1. Tablets may be coated as in Example 1.

We claim:

1. A controlled-release oral dosage form comprising an analgesic-effective amount of acetaminophen, an amount of pseudoephedrine or a pharmaceutically acceptable salt thereof effective in reducing nasal congestion, and an antihistaminic-effective amount of dexbrompheniramine or a pharmaceutically acceptable salt thereof in a single homogeneous matrix, said matrix comprising either (1) a single cellulosic polymer selected from the group consisting of methylcellulose, hydroxypropylcellulose, hydroxymethylcellulose, hydroxyethylcellulose, carboxymethylcellulose, carboxyethylcellulose, sodium carboxymethylcellulose and sodium carboxyethylcellulose; (2) a mixture of said cellulosic, polymers; or (3) said cellulosic polymer or a mixture of said cellulosic polymers and 1 to 45% by weight of the polymer mixture of ethylcellulose or other cellulose ethers or combinations thereof, wherein said single cellulosic polymer or mixture of cellulosic polymers constitutes 1-8% by weight of the uncoated dosage form, or wherein the polymer mixture comprising the cellulose ether constitutes 8-15% by weight of the uncoated dosage form.

2. A dosage form of claim 1 comprising 400 to 750 mg of acetaminophen, 15 to 75 mg of pseudoephedrine sulfate, and 1 to 5 mg of dexbrompheniramine maleate.

3. A dosage form of claim 2 comprising 500 mg of acetaminophen, 60 mg of pseudoephedrine sulfate and 3 mg of dexbrompheniramine maleate.

4. A dosage form of claim 1 comprising 100-55% cellulosic polymers and 0-45% cellulose ether, one or more lubricants selected from stearic acid, magnesium stearate, calcium stearate, waxes, polyethylene glycol and magnesium lauryl sulfate, and one or more fillers selected from dibasic calcium phosphate dihydrate and lactose.

5. A dosage form of claim 4 comprising 100% cellulosic polymer, wherein the total polymer weight represents 1-8% of the total dosage form weight, the total filler weight represents 10-13% of the total dosage-form weight, and the total lubricant weight represents 1-3% of the total dosage form weight.

6. A dosage form of claim 5 wherein the polymer is 100% hydroxypropylcellulose.

7. A dosage form of claim 5 wherein the polymer is 100% hydroxyethylcellulose.

8. A dosage form of claim 5 wherein the filler is dibasic calcium phosphate dihydrate.

9. A dosage form of claim 5 wherein the lubricants are stearic acid and magnesium stearate.

10. A dosage form of claim 5 comprising 1-8% cellulosic polymer, 10-13% dibasic calcium phosphate dihydrate and 1-3% of a combination of stearic acid and magnesium stearate.

11. A dosage form of claim 10 comprising 1-8% hydroxypropylcellulose.

12. A dosage form as claimed in claim 10 comprising 1-8% hydroxyethylcellulose.

13. A dosage form of claim 11 comprising 400 to 750 mg acetaminophen, 15 to 75 mg pseudoephedrine sulfate and 1 to 5 mg dexbrompheniramine maleate.

14. A dosage form of claim 12 comprising 400 to 750 mg acetaminophen, 15 to 75 mg pseudoephedrine sulfate and 1 to 5 mg dexbrompheniramine maleate.

15. A dosage form of claim 4 wherein the polymer comprises 99-55% cellulosic polymer and 1-45% ethylcellulose, the total polymer weight represents 10-15% of the total dosage form weight, the total filler weight represents 10-13% of the total dosage form weight, and the total lubricant weight represents 1-3% of the total dosage form weight.

16. A dosage form of claim 15 wherein the polymer is 66.5-55% cellulosic polymer and 33.5-45% ethylcellulose.

17. A dosage form of claim 15 wherein the filler is dibasic calcium phosphate dihydrate.

18. A dosage form of claim 15 wherein the lubricants are stearic acid and magnesium stearate.

19. A dosage form of claim 15 comprising 66.5-55% cellulosic polymer, 33.5-45% ethylcellulose, 10-13% dibasic calcium phosphate dihydrate and 1-3% of a combination of stearic acid and magnesium stearate.

20. A dosage form of claim 19 comprising 400-750 mg acetaminophen, 15 to 75 mg pseudoephedrine sulfate and 1 to 5 mg dexbrompheniramine maleate.

* * * * *